(12) United States Patent
Kunelius et al.

(10) Patent No.: US 12,303,103 B2
(45) Date of Patent: May 20, 2025

(54) DISPOSABLE SCREW CAP FOR DISPOSABLE LARYNGOSCOPE

(71) Applicant: MedSource International LLC, Chanhassen, MN (US)

(72) Inventors: David Kunelius, Waconia, MN (US); Benjamin Beniek, Richfield, MN (US); Sikandar Hayat, Sialkot (PK)

(73) Assignee: MedSource International LLC

( * ) Notice: Subject to any disclaimer, the term of this patent is extended or adjusted under 35 U.S.C. 154(b) by 373 days.

(21) Appl. No.: 17/474,909

(22) Filed: Sep. 14, 2021

(65) Prior Publication Data
US 2023/0078051 A1   Mar. 16, 2023

(51) Int. Cl.
*A61B 1/00*   (2006.01)
*A61B 1/267*   (2006.01)

(52) U.S. Cl.
CPC ...... *A61B 1/00137* (2013.01); *A61B 1/00066* (2013.01); *A61B 1/00103* (2013.01); *A61B 1/267* (2013.01)

(58) Field of Classification Search
CPC .............. A61B 1/00137; A61B 1/0014; A61B 1/00066; A61B 1/00103; A61B 1/267; B65D 51/16; B65D 51/1644; B65D 51/1661; B65D 2205/00
See application file for complete search history.

(56) References Cited

U.S. PATENT DOCUMENTS

| | | | | |
|---|---|---|---|---|
| 3,598,113 A | * | 8/1971 | Moore | A61B 1/267 600/199 |
| 3,826,248 A | * | 7/1974 | Gobels | A61B 1/267 600/199 |
| 7,946,981 B1 | | 5/2011 | Cubb | |
| 9,986,902 B2 | | 6/2018 | Tydlaska et al. | |
| 10,244,922 B2 | * | 4/2019 | Elbaz | A61B 1/267 |
| 10,849,488 B2 | | 12/2020 | Pecherer | |
| 2004/0242967 A1 | | 12/2004 | Heine et al. | |
| 2008/0096099 A1 | * | 4/2008 | Pecherer | A61B 1/00032 429/96 |
| 2012/0193318 A1 | * | 8/2012 | Meager | B65D 25/40 215/386 |
| 2013/0304116 A1 | * | 11/2013 | Yamane | A61B 1/00137 606/205 |

(Continued)

FOREIGN PATENT DOCUMENTS

| | | |
|---|---|---|
| GB | 2533158 A | 6/2016 |
| WO | 2002/056756 A2 | 7/2002 |
| WO | 2017/189855 A1 | 11/2017 |

*Primary Examiner* — Ellen C Hammond
*Assistant Examiner* — Holly Joanna Lane
(74) *Attorney, Agent, or Firm* — Westman, Champlin & Koehler, P.A.; Amanda M. Prose

(57) ABSTRACT

A disposable laryngoscope with a disposable screw cap. The cap has a base, a perimeter sidewall extending upwardly from the base and an inner surface of the perimeter sidewall having a threads supported thereon, a cavity defined by the perimeter sidewall and base, a tube extending upwardly from the base and positioned within the cavity. A channel is provided in the cavity between an outer perimeter of the tube and the threads on the inner surface of the perimeter side wall. The disposable screw cap threadedly connects to the handle of the laryngoscope to provide access to the interior cavity of the handle.

9 Claims, 3 Drawing Sheets

(56) References Cited

U.S. PATENT DOCUMENTS

| | | | |
|---|---|---|---|
| 2014/0001186 A1* | 1/2014 | Boyd | B65D 51/16 |
| | | | 220/367.1 |
| 2018/0168433 A1* | 6/2018 | Meyer | A61B 1/00016 |
| 2023/0165455 A1* | 6/2023 | Kunelius | A61B 1/267 |
| | | | 600/190 |

* cited by examiner

DISPOSABLE SCREW CAP FOR DISPOSABLE LARYNGOSCOPE

BACKGROUND

The present invention relates to a disposable laryngoscope.

Laryngoscopes are intended to illuminate the larynx or vocal cords for visual inspections. One style of the laryngoscope can be inserted into the patient's mouth to hold down the patient's tongue for a clear view of the patient's throat.

The demand for disposable medical supplies has grown, spurred by the increase in geriatric patients and expanded insurance coverage from the Patient Protection and Affordable Care Act in the U.S. Healthcare organizations have turned to disposables as a response to increased pressure from federal, accreditation organizations and other regulatory bodies to prevent patient and staff harms.

The primary reason for creating disposable devices is infection control. When an item is used only once by a caregiver, it cannot transmit infectious agents to subsequent patients.

While an obvious factor in the design of single-use products could be considered cost, given the nature of medical devices, disposable medical devices require a careful balance between performance, cost, reliability, materials, and shelf life.

Currently, disposable-device assembly depends primarily on injection-molded plastic pieces and/or assembly by bonding, gluing, ultrasonic welding or radio-frequency welding. The high production volume of single-use devices calls for an automated assembly in clean rooms to minimize human contact. Unlike reusable devices, which are often sterilized at the healthcare facility, disposable devices are sterilized before leaving a manufacturing site and are thus provided in a ready-to-use state.

The handle of a laryngoscope supports operational components of the laryngoscope such as a battery assembly including a blade contact assembly with a battery assembly including a battery, battery spring and contact spring such that power to a light source on a blade for the laryngoscope can be illuminated with use of the laryngoscope.

SUMMARY

An aspect of the present disclosure relates to a disposable screw cap for a laryngoscope handle. The disposable cap has a base and a perimeter sidewall extending upwardly from the base and an inner surface of the perimeter sidewall having a threads supported thereon where a cavity is defined by the perimeter sidewall and base. The cap further has a tube extending upwardly from the base and positioned within the cavity. A channel is provided in the cavity between an outer perimeter of the tube and the threads on the inner surface of the perimeter side wall.

The tube extends upwardly from the base and has a length that extends beyond a height of the perimeter sidewall. The tube extends upwardly a distance in the range of 1.5 to 2 times the height of the perimeter side wall. The tube is substantially hollow.

The cap is comprised of a hard plastic material.

The cap has a diameter and a thread length sufficient to screwably couple the cap to a handle of a laryngoscope.

Yet another aspect of the present disclosure relates to a disposable laryngoscope with a handle having an externally threaded end and wherein access to an interior cavity of the handle is provided through an opening in the threaded end and a cap having a base and a perimeter sidewall extending upwardly from the base wherein the cap has an internally threaded length, a cavity defined by the perimeter sidewall and base; and a tube extending upwardly from the base and positioned within the cavity. A channel is provided in the cavity between an outer perimeter of the tube and the threads on the inner surface of the perimeter side wall. The cap is a screw cap that is removably connectable to the handle.

The tube of the cap fits into the interior cavity of the handle and the externally threaded end of the handle threadably secures to the internal threads of the cap.

One or both of the handle and the cap are comprised of a plastic.

A thickness of the externally threaded end fits into the channel provided in the cavity of the cap when the cap is screwed onto the handle.

DETAILED DESCRIPTION

Figure 2:
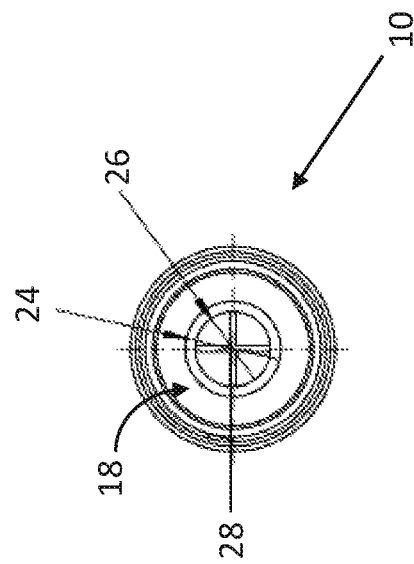
FIG. 2 is a bottom view of the disposable cap.
Figure 1:
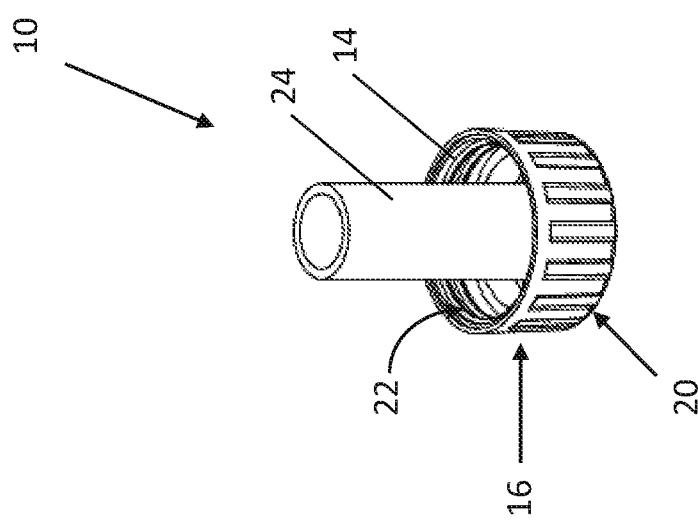
FIG. 1 is a perspective view of a disposable cap for a laryngoscope.
Figure 4:
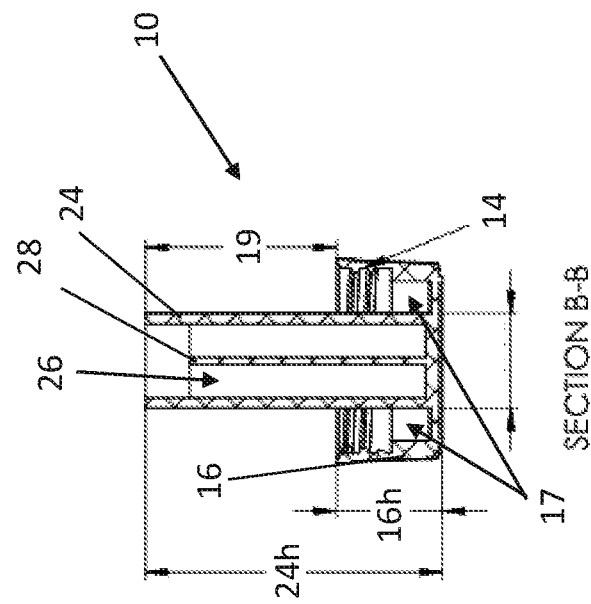
FIG. 4 is a cross-sectional view of the disposable cap along B shown in FIG. 3.
Figure 3:
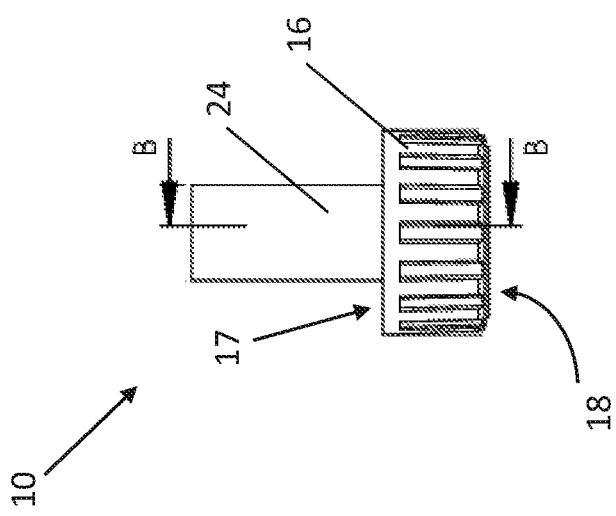
FIG. 3 is a side view of the disposable cap.

A disposable cap described herein is configured for use with a disposable laryngoscope handle. Thus, the disposable cap allows for the entire laryngoscope assembly to be a single use, disposable assembly. The disposable cap is a screw cap that is configured for easy connection to the laryngoscope handle and to provide access to the inner components of the laryngoscope handle with ease. The disposable cap may have an internally threaded length to engage with external threads on a base of the handle opposite a blade mounting end of the handle. The disposable cap is thus a "screw cap".

The disposable laryngoscope cap described herein further comprises a center extended portion which extends into the body of the handle when the cap is secured to the handle. This extended portion may provide a back force to a battery within the laryngoscope to force contact between a battery a light source to power the light source of the laryngoscope blade.

The cap and handle described herein are disposable, wherein the disposable handle is provided with an access point by way of the removable cap, providing an entirely disposable device retaining access to an interior opening in the handle and components stored therein.

A disposable cap 10 for a laryngoscope handle 12 is illustrated generally in FIGS. 1-4. The disposable cap 10 is an internally threaded closure for the handle 12 and is configured to screw onto an end 36 of the handle 12 of the laryngoscope. The end 36 of the handle 12 is externally threaded for securing the cap 10 to the handle 12.

The cap 10 has a perimeter wall 16 extending upwardly from a base 18 of the cap 10. The perimeter wall 16 and base 18 arrangement provides the cap 10 with an open interior space or cavity 17 for receiving the end 36 of the handle 12. The perimeter wall 16 may have an external texture 20 for gripping of the cap 10 to aid in screwing the cap 10 on to the handle 12 and unscrewing the cap 10 therefrom. An interior surface 22 of the perimeter wall 16 supports threads 14 thereon. Extending upwardly from the base 18 within the cavity 17 is a center extension 24.

The center extension 24 may be a tube having a length that extends beyond or above the perimeter wall 16. The center extension 24 may be substantially circular in cross-section and with a hollow open space 26 substantially along its length. A prong 28 may extend upwardly from the base 18 and be positioned within the open space 26. A length of the prong 28 may be less than, about equal to, or greater than the length of the extension 24. The prong 28 may comprise two lengths 28 that extend across different inner diameters of the extension 24 and thus crossing in the middle of the open space 26.

The cap 10 may be comprised of a hard plastic and may be formed as a unitary, monolithic structure. For example, the cap may be formed by injection molding, 3D printing, or other manufacturing processes.

The cap 10 may be provided in various size configurations. In one embodiment, the perimeter wall 16 has a height 16$h$ and the center extension 24 has a height 24$h$ that is greater than the wall height 16$h$. The height 24$h$ of the center extension 24 may be in the range of 2.5 to three times that of the height 16$h$ of the perimeter wall. Additionally, or alternatively, the height 24$h$ of the center extension 24 extends beyond the perimeter wall 16 by a distance 19 that may be 1.5 to two times the height 16$h$ of the perimeter wall 16. For example, the perimeter wall 16 may have a height of 15.5 mm measured from the outer surface of the base 18 of the cap 10 and the center extension 24 having a height of 43.5 mm measured from the same surface such that the center extension extends beyond the height 16 of the perimeter wall 16 by approximately 28 mm.

A thickness of the center extension may be about $1/10^{th}$ the diameter of the cap 10 such that a 30 mm cap 10 has a center extension 24 with a wall thickness of 3 mm such that a space is provided between the perimeter wall 16 and the center extension 24 and a space is provided within the center extension 24. In the embodiment illustrated the cap 10 is substantially round and the center extension 24 is also substantially round.

Figure 5:
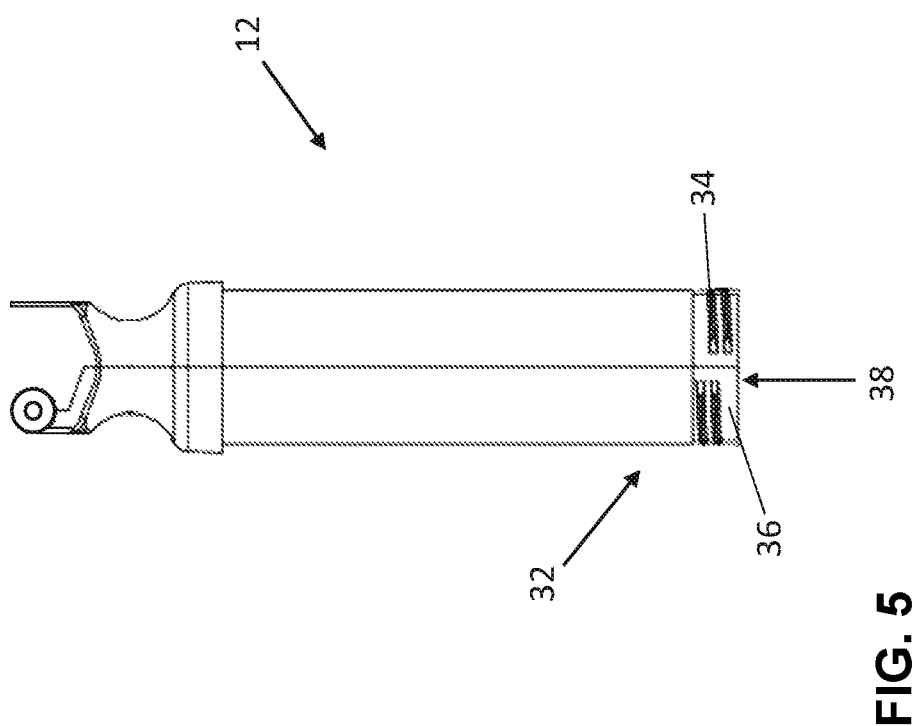
FIG. 5 is a side view of a laryngoscope configured to receive the disposable cap.

The disposable laryngoscope handle 12 for connecting with the cap 10 is illustrated in FIG. 5. The handle 12 has a distal end 32 which is configured for connecting to the cap 10. The distal end 32 has a portion supporting external threads 34 for threaded connection with threads 14 of the cap. Dimensions of the distal end 32 are sufficient such that the threaded end 36 with threads 34 fits into the cap 10 so the threads 14 and 34 threadably mate as the cap 10 is screwed thereon and the threaded end 36 is open at its terminal end, providing access to an inner cavity 38 of the handle 12 and any operational or power components supported inside the handle 12 cavity 38. The threaded end 36 is configured such that the center extension 24 fits within the cavity 38 of the handle 12 as the cap 10 is screwed into connection with the handle 12.

The entire laryngoscope assembly is disposable and can be a single use device.

Although the present disclosure has been described with reference to preferred embodiments, workers skilled in the art will recognize that changes may be made in form and detail without departing from the spirit and scope of the disclosure.

The invention claimed is:

1. A disposable screw cap for a laryngoscope handle, the disposable cap comprising:
   a base;
   a perimeter sidewall extending upwardly from the base and an inner surface of the perimeter sidewall having a thread supported thereon;
   a cavity defined by the perimeter sidewall and base;
   a tube extending upwardly from the base and positioned centrally on the base and within the cavity, the tube co-extending upwardly from the base with the perimeter sidewall and extending to a height greater than the height of the perimeter sidewall;
   a prong extending upwardly from the base and positioned centrally on the base and within the tube, and
   wherein a channel is provided in the cavity between an outer perimeter of the tube and the threads on the inner surface of the perimeter side wall such that the channel surrounds the outer perimeter of the tube.

2. The disposable screw cap of claim 1 wherein the tube extends upwardly a distance in the range of 1.5 to 2 times the height of the perimeter side wall.

3. The disposable screw cap of claim 1 wherein the tube is substantially hollow.

4. The disposable screw cap of claim 1 wherein the cap is comprised of a hard plastic material.

5. The disposable screw cap of claim 1 wherein the cap has a diameter and a thread length sufficient to screwably couple the cap to a handle of a laryngoscope.

6. A disposable laryngoscope comprising:
   a handle having an externally threaded end and wherein access to an interior cavity of the handle is provided through an opening in the threaded end;
   a cap comprising:
      a base and a perimeter sidewall extending upwardly from the base wherein the cap has an internally threaded length;
      a cavity defined by the perimeter sidewall and base; and
      a tube extending upwardly from the base to an extent greater than the perimeter side wall and the tube positioned within the cavity, and
      wherein a channel is provided in the cavity between an outer perimeter of the tube and the threads on the inner surface of the perimeter side wall,
   wherein the cap is a screw cap that is removably connectable to the handle, and
   wherein the tube provides a back force to a battery within the laryngoscope to force contact between a battery and a light source to power the light source of the laryngoscope.

7. The laryngoscope of claim 6 wherein the tube of the cap fits into the interior cavity of the handle and the externally threaded end of the handle threadably secures to the internal threads of the cap.

8. The laryngoscope of claim 6 wherein one or both of the handle and the cap are comprised of a plastic.

9. The laryngoscope of claim 6 wherein a thickness of the externally threaded end fits into the channel provided in the cavity of the cap when the cap is screwed onto the handle.

* * * * *